(12) United States Patent
Hayashi et al.

(10) Patent No.: US 10,113,954 B2
(45) Date of Patent: Oct. 30, 2018

(54) GAS SENSOR BY LIGHT ABSORPTION

(71) Applicant: KONINKLIJKE PHILIPS N.V., Eindhoven (NL)

(72) Inventors: Daiyu Hayashi, Cologne (DE); Achim Hilgers, Alsdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 19 days.

(21) Appl. No.: 15/110,191

(22) PCT Filed: Dec. 11, 2014

(86) PCT No.: PCT/EP2014/077425
§ 371 (c)(1),
(2) Date: Jul. 7, 2016

(87) PCT Pub. No.: WO2015/104133
PCT Pub. Date: Jul. 16, 2015

(65) Prior Publication Data
US 2016/0327475 A1    Nov. 10, 2016

(30) Foreign Application Priority Data
Jan. 7, 2014    (EP) .................... 14150285

(51) Int. Cl.
*G01N 21/35*    (2014.01)
*G01N 21/3504*    (2014.01)
*G01N 21/03*    (2006.01)
*G01N 21/33*    (2006.01)
*G01N 21/359*    (2014.01)

(52) U.S. Cl.
CPC ....... *G01N 21/3504* (2013.01); *G01N 21/031* (2013.01); *G01N 21/33* (2013.01); *G01N 21/359* (2013.01); *G01N 2201/062* (2013.01); *G01N 2201/06113* (2013.01)

(58) Field of Classification Search
CPC .................................................. G01N 21/3504
See application file for complete search history.

(56) References Cited

U.S. PATENT DOCUMENTS

| 3,811,776 | A | * | 5/1974 | Blau, Jr. ............ G01N 21/3518 250/343 |
| 5,625,189 | A | | 4/1997 | McCaul et al. |
| 6,091,504 | A | * | 7/2000 | Walker ................... G01N 21/39 250/343 |
| 6,603,555 | B1 | | 8/2003 | Nanami et al. |
| 7,715,010 | B2 | | 5/2010 | Rawis et al. |
| 9,035,256 | B2 | | 5/2015 | Gibson et al. |

(Continued)

OTHER PUBLICATIONS

Ristic, L., "Sensor Technology & Devices" (Optoelectronics Library) Artech House, Inc. 1994, Richard S. Quimby, Photonics and Lasers: An Introduction; John Wiley & Sons, 2006.

(Continued)

*Primary Examiner* — Casey Bryant

(57) ABSTRACT

The present invention relates to an absorption spectroscopy device, comprising a light cavity vessel (1) whose inner wall is at least partially coated with a light reflective layer (2), wherein said light reflective layer is a distributed Bragg reflector or is composed of stainless steel or aluminium; a photo-detector; and a light source, wherein said light source is capable of emitting light radiation which passes through said light cavity vessel, wherein said light cavity vessel is capable of reflecting the emitted radiation and wherein said photo-detector is capable of detecting at least a portion of the emitted light.

19 Claims, 1 Drawing Sheet

(56) References Cited

U.S. PATENT DOCUMENTS

| | | |
|---|---|---|
| 2005/0286054 A1 | 12/2005 | Chen et al. |
| 2009/0235720 A1 | 9/2009 | Smith |
| 2011/0124987 A1* | 5/2011 | Papazoglou ......... A61B 5/0059 600/310 |
| 2013/0270429 A1 | 10/2013 | Bilenko et al. |
| 2014/0185042 A1* | 7/2014 | Baets ................... G01N 21/658 356/301 |
| 2015/0077747 A1 | 3/2015 | Smith |
| 2015/0103343 A1* | 4/2015 | Smith ...................... G01J 3/26 356/326 |

OTHER PUBLICATIONS

Seinfeld, J.H. et al., "Atmospheric Chemistry and Physics; From Air Pollution to Climate Change", John Wiley & Sons, 2006., ISBN: 978-0-471-72018-8.
Herbst, J. et al., "Compact Multi Reflection Cells for Optical Gas Sensor Applications", Sensor + Test Conference 2009—IRS' 2009 Proceedings, pp. 255 + 256.
Jenkins; T.P. et al., "Diode laser absorption for detecting oxygen in head space of vials", ICCC Sensors 2008 Conference, pp. 266-269.
Kroll, M. et al., "Measurement of Gaseous Oxygen using Diode Laser Spectroscopy", Appl. Phys Let., 51 (18) 1987, pp. 1465-1467.
Philippe, L.C., et al., "Laser Diode Wavelength-Modulation Spectroscopy for Simultaneous Measurement of Temperature, Pressure, adn Belocity in Shock Heated Oxygen Rows", Appl. Opt. 32 (30) 1993, pp. 6090-6103.
Weldon, V., et al., "Oxygen Sensing Using Single Frequency GaAs-AlGaAs DFB Laser Diodes and VCSELs", Electronics Letters 32 (3) 1996, pp. 219-221.

* cited by examiner

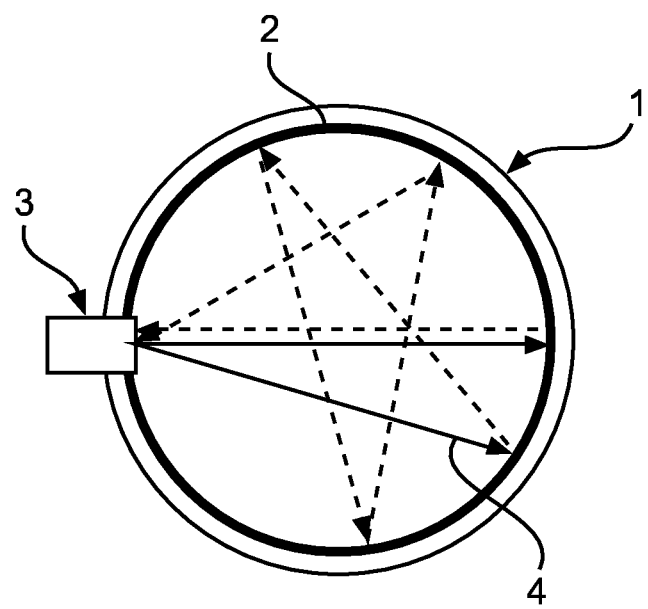

GAS SENSOR BY LIGHT ABSORPTION

This application is a national stage application under 35 U.S.C. § 371 of International Application No. PCT/EP2014/077425 filed on Dec. 11, 2014 and published in the English language on Jul. 16, 2015 as International Publication No. WO/2015/104133, which claims priority to European Patent Application No. 14150285.6 filed on Jan. 7, 2014, the entire disclosures of which are incorporated herein by reference.

FIELD OF THE INVENTION

The present invention relates to an absorption spectroscopy device, comprising a light cavity vessel, whose inner wall is at least partially light reflective; a photodetector; and a light source, wherein said light source is capable of emitting light radiation which passes through said light cavity vessel, wherein said light cavity vessel is capable of reflecting the emitted radiation and wherein said photodetector is capable of detecting at least a portion of the emitted light. The present invention also relates to a method for spectroscopically measuring the concentration of a gas, preferably $O_2$, comprising the steps: (a) emitting light radiation which passes through a light cavity vessel comprising the gas, wherein said light radiation is at least partially reflected by the inner wall of said cavity vessel; (b) detecting at least a portion of the emitted light with a photodetector; and (c) determining radiation absorption of said gas on-airway by comparison of the detected light with a reference measurement carried out according to steps (a) and (b) with (i) a defined amount of said gas and (ii) without said gas.

BACKGROUND OF THE INVENTION

Oxygen is known as one of the most important gaseous species for the lifecycle of a human being. Its presence and concentration is of high relevance in many fields, including health care, food industry, security etc. High precision oxygen sensors are therefore much sought-after.

Different molecules absorb electro-magnetic radiation typically in dependence of the frequencies of the radiation. Thus, particular molecules have a unique absorption spectrum versus the used radiation frequency, which allows for a specific absorption determination, and thus measurement of the concentration of the molecules. In the case of oxygen molecules the ground state of the molecule is $X^3S_g^-$ which can be excited to low-lying excited states of $a^1D_g$, $b^1S_g^+$, $c^1S_u^-C^3D_u$, $B^3S_u^-$. The dipole transitions between the ground state to all the low-lying excited states are forbidden, so that the ground state of oxygen molecules shows a weak light absorption in the wavelength range from 300-1200 nm.

Methods for measuring the concentration of ground state oxygen molecules have been described, e.g. by Kroll et al., Appl. Phys. Lett., 51 (18) 1987, 1465-1467 or Philippe and Hanson, Appl. Opt. 32 (30) 1993, 6090-6103. In these methods, typically, the weak band transition of $b^1S_g^+-X^3S_g^-$ locating around 760 nm is employed for optical absorption spectroscopy to measure the oxygen molecular concentration. As a light source for the absorption, an IR laser at the central wavelength of 760 nm can be utilized, and a photodiode at the corresponding wavelength may be used for the detection of the laser intensity after the absorption. The laser light may accordingly be introduced into a gaseous environment containing oxygen molecules. While the laser light is transmitted through the environment, photons of the laser light are absorbed by the ground-state oxygen molecules ($X^3S_g^-$) by the weak band transition of $b^1S_g^+-X^3S_g^-$. This results in a decrease of the laser intensity. The concentration of the oxygen molecules in the ground state ($X^3S_g^-$) can subsequently be determined by comparing the decreased laser intensity to the initial laser intensity or an equivalent control laser intensity in the absence of gaseous molecules. The intensity decrease of the laser light, which can be determined in such a laser absorption sensor, is typically proportional to the length of the laser path (L).

In practical implementations of these laser absorption sensors, it may be advantageous to miniaturize the geometric size of the sensor device. However, by reducing the size of the device, also the length of the laser path (L) decreases, at least if only a single-path laser absorption is used. A possible solution to this problem is the employment of multi-path laser absorption, in which the laser light is reflected multiple times by mirrors until the laser light is detected by a photodiode. The effective length ($L_{eff}$) of the laser path is then multiplied by the times of the reflection (n), as $$L_{eff}=n \times L_{geo} \quad \text{Formula (1)}$$

where $L_{geo}$ is the geometric length of the distance between the laser and the mirror(s).

Currently known laser absorption sensors are based on a laser as light source of 760 nm radiation and a photodiode for the detection. They typically use single-path absorption, so that the detection limit becomes larger when the dimension of the sensor becomes smaller. In these cases the requirement of the detection limit may not be fulfilled. In addition, by miniaturizing the laser absorption sensors, e.g. to the range of a few cm, space may become restricted so that it becomes difficult to use separate light sources and photodiodes in a setup.

In consequence, there is a need for the development of an improved absorption spectroscopy device for gas measurement applications in a miniaturized format.

OBJECTS AND SUMMARY OF THE INVENTION

The present invention addresses these needs and provides means and methods for spectroscopically measuring gas concentrations, in particular oxygen concentrations, even at small geometric sizes. The above objective is in particular accomplished by an absorption spectroscopy device, comprising: a light cavity vessel, whose inner wall is at least partially light reflective; a photodetector; and a light source, wherein said light source is capable of emitting light radiation which passes through said light cavity vessel, wherein said light cavity vessel is capable of reflecting the emitted radiation and wherein said photodetector is capable of detecting at least a portion of the emitted light. In particular, it was surprisingly found by the inventors that by using a light cavity vessel without a concretely defined mirror configuration and a predetermined light path, light can be scattered all over the light cavity vessel due its light reflective inner wall. I.e. photons derived from the light source are reflected back by the inner wall of the cavity, reflected photons hit the reflective inner wall again etc. and thus reflected multiple times in the light vessel. The light may accordingly fill all the geometric space of the cavity, i.e. fill the light cavity vessel with geometrically homogenous intensity and thus provide for an infinite length path for light absorption. A part of the emitted light will eventually hit the photodetector and can accordingly be measured. Based on this approach it is no longer necessary to exactly determine the length of the lightpath. In contrast to a single path absorption as known from the prior art the inventive device allows to achieve higher absorbance, which results in a lower detection limit of the oxygen molecule's concentration. This allows for the detection of even low or very low gas concentrations or of small changes to existing gas concentrations.

In a preferred embodiment of the present invention the light source of the device is a light emitting diode or a laser.

In a further preferred embodiment said inner wall of the light cavity vessel is at least partially coated with a light reflective layer.

In a particularly preferred embodiment said light reflective layer is a distributed Bragg reflector or is composed of stainless steel or aluminium. The distributed Bragg reflector may comprise, in specific embodiments, layers of $SiO_2$ and $TiO_2$; $SiO_2$ and $ZrO_2$; SiC and MgO; SiC and Silica; GaAs and AlAs; ITO; or a-Si and a-Si.

In another preferred embodiment the distributed Bragg reflector may be reflective for the radiation corresponding to the electronic transitions of oxygen molecules from the ground electronic state ($X^3\Sigma_g^-$) to the electronic excited states ($a^1\Delta_g$, $b^1\Sigma_g$), wherein the wavelength of said radiation is at about 343.4 nm, 360.5 nm, 380.2 nm, 446.7 nm, 477.3 nm, 532.2 nm, 630.0 nm, 687.2 nm, 689.3 nm, 760.8 nm, 763.8 nm, or1065.2 nm as the center wavelength within a variation of the wavelength of ±10 nm.

In yet another preferred embodiment said light source may be a light emitting diode or a laser diode of UV-A radiation, UV-B radiation, of visible radiation or of infrared radiation.

In a particularly preferred embodiment the light source is a vertical-cavity surface-emitting laser (VCSEL) diode. The VCSEL diode may, in specific embodiments, emit laser radiation around the wavelength of about 687.2 nm, 689.3 nm, 760.8 nm, or 763.8 nm within the variation of the wavelength of ±10 nm.

In a particular embodiment the VCSEL diode may be part of a laser package which additionally comprises the photodiode as integrated element.

In a particularly preferred embodiment, the device is adapted to measure a gas, preferably $O_2$.

In a further aspect the present invention relates to a method for spectroscopically measuring the concentration of a gas, preferably $O_2$, comprising the steps:

(a) emitting light radiation which passes through a light cavity vessel comprising the gas, wherein said light radiation is at least partially reflected by the inner wall of said cavity vessel; (b) detecting at least a portion of the emitted light with a photodetector; and (c) determining radiation absorption of said gas on-airway by comparison of the detected light with a reference measurement carried out according to steps (a) and (b) with (i) a defined amount of said gas and (ii) without said gas.

In preferred embodiment of the method as defined above the light radiation is the radiation from a light emitting diode or laser around the wavelength of 687.2 nm, 689.3 nm, 760.8 nm, or 763.8 nm within the variation of the wavelength of ±10 nm, preferably a laser radiation around the wavelength of 687.2 nm, 689.3 nm, 760.8 nm, or 763.8 nm within the variation of the wavelength of ±10 nm.

In a particularly preferred embodiment the method may be carried out in a device as defined herein above.

In another preferred embodiment of the present invention the reference measurements are linked to the specific device in which they were carried out. In yet another preferred embodiment, the reference measurements are optionally stored for further gas concentration measurements according to steps (a) and (b).

BRIEF DESCRIPTION OF THE DRAWINGS

FIG. 1 shows a light cavity vessel in a circular form according to an embodiment of the present invention.

DETAILED DESCRIPTION OF THE EMBODIMENTS

The present invention relates to an absorption spectroscopy device, comprising: a light cavity vessel, whose inner wall is at least partially light reflective; a photo-detector; and a light source.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%, unless defined otherwise.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect an absorption spectroscopy device, comprising: a light cavity vessel, whose inner wall is at least partially light reflective; a photo-detector; and a light source, wherein said light source is capable of emitting light radiation which passes through said light cavity vessel, wherein said light cavity vessel is capable of reflecting the emitted radiation and wherein said photo-detector is capable of detecting at least a portion of the emitted light.

The term "light cavity vessel" as used herein refers to a cylindrical, spherical or hemispherical entity which is capable of reflecting light in interior points, e.g. at its inner walls. The light cavity vessel may have convex walls, whose inclination or curvature throughout the vessel is identical, essentially identical or may vary, e.g. the cavity vessel may be composed of differentially formed curvatures, or differently formed spherical or elliptical or semi-elliptical portions. In a preferred embodiment, the light cavity vessel is a perfect sphere. The light cavity vessel may have a diameter or characteristic geometrical size of about 0.1 cm, 0.2 cm, 0.3 cm, 0.4 cm, 0.5 cm, 0.6 cm, 0.7 cm, 0.8 cm, 0.9 cm, 1 cm or more than 1 cm, e.g. 2 cm, 3 cm, 4 cm, 5 cm, 6 cm, 7 cm, 8 cm, 9 cm, 10 cm, 15 cm, 20 cm, 30 cm, 40 cm, 50 cm, 60 cm, 70 cm, 80 cm, 90 cm, 100 cm or more than 100 cm or any value in between these values. Further envisaged are light cavity vessels, which a diameter of less than 1 cm. In case the light cavity vessel is not entirely spherical, the term "diameter" as used herein refers to the longest axis of the vessel.

In preferred embodiments the light cavity vessel may have a diameter or a characteristic geometrical size of less than 10 cm, more preferably of less than 1 cm. Particularly preferred is a diameter of about 0.1 to 2 cm.

The cavity vessel typically shows no edges or angles at interior walls. In specific embodiments, the light cavity vessel is adapted to comprise gaseous substances, in particular oxygen ($O_2$). The light cavity vessel may accordingly be provided with a gas inlet, and optionally a gas outlet structure. Furthermore, the light cavity structure may be provided in a gas tight manner, e.g. it may comprise a locking structure which, upon the entrance of gaseous substances to be measured, allows a closing of the cavity vessel at least during the absorption spectroscopy measurement. In further embodiments, the light cavity vessel may be adapted to the measurement of a continuous gaseous entry and exit, e.g. in the form of a respiratory filling and emptying by a patient during bedside surveillance of oxygen concentration. Alternatively, the light cavity vessel may be adapted to non-medical uses. For example, the light cavity vessel may be adapted to combustion engine control or combustion optimization. The light cavity vessel may accordingly be adapted to a function of a lambda sensor in a gas or liquid being analyzed, e.g. to measure the exhaust gas concentration of oxygen for internal combustion engines in automobiles and other vehicles. In a further alternative, the light cavity vessel may be adapted to measurements in diving equipment, e.g. in order to measure the partial pressure of oxygen in the breathing gas.

The light cavity vessel is at least partially light reflective. The term "light reflective" as used herein means that light which is emitted from a light source in the cavity vessel is reflected by the inner wall of the cavity vessel. The reflection may be a reflection of the entire light beam or amounts of photons reaching the wall, or of a considerable amount of the light beam or photons, e.g. 99.99%, 99.9%, 99%, 98%, 97%, 96%, 95%, 94%, 93%, 92%, 91%, or about 90%. Also lower degree or efficiency of refection is possible. In case a reduced reflection efficiency is given, this effect may be compensated by increasing the sensitivity of the photodetector as described herein. The light reflection may be a specular or a diffuse reflection. Incoming light beams may, according to the form of the cavity vessel and the angel of the light beam, be reflected in a singular manner, or reflected in multiple ways. Due to the spherical or semi-spherical form of the cavity vessel, the reflection at a first point of the inner wall of the cavity vessel may lead to a further reflection at a second point of the inner wall of the cavity vessel, followed by a further reflection at a third point of the inner wall of the cavity vessel etc. This may potentially lead to multiple reflection events and a filling of all the geometric space of the cavity, while a certain percentage of the reflected radiation may hit a photo-detector as defined herein.

The term "partially" as used in the context of the light reflection in the cavity vessel means that light which enters the cavity vessel may be reflected by most interior parts or sectors e.g. walls, but not necessary all interior parts or sectors of the light cavity vessel. Some sectors of the light cavity vessel may not be light reflective, e.g. the light source itself may not be light reflective, or a detection unit which allows detecting reflected light, e.g. a photo-detector may not be light reflective. Furthermore, inlet and/or outlet structures, power supply or control elements etc. may not be light reflective. In specific embodiments, the "partial reflection" may also include a reflection of only a specific wavelength or range of wavelengths, while other wavelengths or ranges of wavelengths are not reflected, but absorbed by the light cavity vessel inner wall(s). Such selective reflection may, for example, be used to filter out non-exciting or spectroscopically non-functional wavelengths. In specific embodiments, the at least partially light reflecting inner wall of a light cavity vessel as defined herein may be coated with a light reflecting layer. This coating may be a complete or a partial coating of the inner wall of the light cavity vessel. For example, the coating may be provided in all sectors of the light cavity vessel, except for the sector of the light source and the photo-detector sector. In further embodiments, other sectors may be excluded from a coating with a light reflecting layer, e.g. inlet or outlet structures, control elements etc.

The light reflective layer may be composed of any suitable light reflective material. For example, the light reflective layer may be composed of stainless steel, aluminum, silver, copper, gold, platinum, antimony, cadmium, nickel, tin, quicksilver, or other brilliant material.

In specific embodiments, the light reflective layer may be a distributed Bragg reflector (DBR). The term "distributed Bragg reflector" as used herein refers to reflector element having a structure formed from multiple layers of alternating materials with varying refractive index, or by periodic variation of some characteristic (such as height) of a dielectric waveguide, resulting in periodic variation in the effective refractive index in the guide. Each layer boundary may typically cause a partial reflection of an optical wave. In particular, waves whose wavelength may be near four times the optical thickness of the layers, may provide many reflections which combine with constructive interference. The layer may accordingly act as a high-quality reflector. Suitable DBR layer may comprise layers of $SiO_2$ and $TiO_2$; $SiO_2$ and $ZrO_2$; SiC and MgO; SiC and Silica; GaAs and AlAs; ITO; or a-Si and a-Si. The layers may preferably have a thickness of less than 1 mm, less than 0.5 mm, particularly less than 0.2 mm. Further details would be known to the skilled person or can be derived from suitable literature sources such as the Handbook of Optics IV, Bass, Li and Stryland ed., McGraw-Hill, $3^{rd}$ edition, 2009.

In preferred embodiment the distributed Bragg reflector may be reflective for the radiation corresponding to the electronic transitions of oxygen molecules from the ground electronic state ($X^3\Sigma_g^-$) to the electronic excited states ($a^1\Delta_g$, $b^1\Sigma_g^+$). The distributed Bragg reflector may accordingly be adapted to radiation emission from a laser or LED as defined herein, preferably radiation emission wherein said radiation corresponds to the electronic transitions of oxygen molecules from the ground electronic state ($X^3\Sigma_g^-$) to the electronic excited states ($a^1\Delta_g$, $b^1\Sigma_g^-$). Examples of radiation corresponding to the electronic transitions of oxygen molecules from the ground electronic state ($X^3\Sigma_g^-$) to the electronic excited states ($a^1\Delta_g$, $b^1\Sigma_g^-$), where are also the preferred reflected wavelengths of the DBRs are 343.4 nm, 360.5 nm, 380.2 nm, 446.7 nm, 477.3 nm, 532.2 nm, 630.0 nm, 687.2 nm, 689.3 nm, 760.8 nm, 763.8 nm, or 1065.2 nm as the center wavelength within a variation of the wavelength of ±10 nm. The term "center wavelength" as used herein means that the reflected wavelength may vary in a range around the indicated value. The range may, in certain embodiments, a range of ±10 nm, e.g. in case of 343.4 nm a range between 333.4 nm and 353.4 nm. In specific embodiments, the wavelengths may vary by different ranges such as, e.g., by about ±8 nm, ±6 nm, ±5 nm, ±4 nm, ±3 nm, ±2 nm, or ±1 nm. It is particularly preferred that the reflected wavelengths of the DBRs are in the range of 687.2 nm ±10 nm, 689.3 nm ±10 nm, 760.8 nm ±10 nm, 763.8 nm ±10 nm. Even more preferred is the reflection of a wavelength range of 760.8 nm ±10 nm. Further envisaged are more narrow ranges around 687.2 nm, 689.3 nm, 760.8 nm, and 763.8 nm such as, e.g., by ranges of about ±8 nm, ±6 nm, ±5 nm, ±4 nm, ±3 nm, ±2 nm, or ±1 nm.

In specific embodiments, DBRs of two or more different materials may be combined in one light cavity vessel. In further embodiments, the DBRs may be provided with different center wavelengths at different sectors or portions, e.g. at different hemispheres of a spherical light cavity vessel. For instance, such DBRs may used in combination with one or more suitable photodetectors, e.g. a photodetector which is capable of detecting more than one wavelength, or two or more photodetectors, which are capable of detecting different wavelengths. The wavelengths detected by the photodetector(s) and reflected the different DBRs may further be adapted to each other. A "light source" as mentioned herein is any suitable light source, which provides light in a wavelength and intensity allowing to be used for spectroscopic absorption measurements. The light source may be placed in the light cavity vessel such that light radiation is emitted into said light cavity vessel. The emission of the light radiation may be one specific direction or angle, or it may be an emission in more than one direction or at more than one angle. The emission in more than one direction or at more than one angle may lead to a filling of the light cavity vessel with light with a geometrically homogenous intensity. In specific embodiments, more than one light source may be provided in a device as defined herein, i.e. more than one light source may be connected with one light cavity vessel as defined herein. In case more than one light source is provided in a device, the light sources may emit radiation of the same or, preferably, of different wavelengths. By emitting light of different wavelengths, the absorption of different gas molecules may be performed at the same time. Alternatively, a second or further wavelength in a second or further light source may be used for reference or control measurements of a gas molecule whose concentration is to be determined. For example, such second or further light sources may emit radiation which is not an absorption radiation of the gas molecule whose concentration is to be determined. In further embodiments, such a second or further radiation may alternatively also be provided by a single light source, e.g. a light source which is tunable or allows the production of different wavelength emissions.

In specific embodiments, the light source might be a laser, i.e. a device that emits light through a process of optical amplification based on the stimulated emission of electromagnetic radiation. The laser typically emits light coherently thus allowing a laser beam to stay narrow over long distances. Laser beams to be used in the context of the present invention may have a high spatial coherence, e.g. in the range of high temporal or longitudinal coherence, i.e. a relatively large coherence length along its beam, e.g. of longer than the characteristic geometrical length of the cavity. The laser may be a multiple or single wavelength laser. Preferred is a single wavelength laser. The laser may further be a laser emitting light of single polarization or of multiple polarizations. Preferred is a laser emitting light of a single polarization. In further embodiments, the laser may operated in a continuous mode, or be operated in a pulsed mode. Typically, a laser may provide a continuous wave, i.e. produce a beam output whose power is constant over time. Alternatively, pulsed mode may be provided by lasers providing optical power in pulses of some duration at certain repetition rates. Lasers to be used in the context of the present invention may have an energy output of about 5 mW or more, e.g. 10 mW, 100 mW, 500 mW up to 1 W.

Examples of suitable laser include gas lasers, e.g. a helium-neon laser, a carbon dioxide laser, a carbon monoxide laser, an argon-ion laser, a TEA laser, a copper laser such as a Cu vapor laser, or a Cu—Br vapor laser, a metal ion laser such as a He—Ag laser, a He—Cd laser or a Ne—Cu laser.

Further examples are excimer lasers, i.e. gas lasers which are powered by a chemical reaction involving an excited dimer form of two atoms such as XeF.

Further examples of suitable lasers include chemical lasers such as hydrogen fluoride lasers, deuterium fluoride lasers, or oxygen-iodine lasers.

Preferred examples of lasers are solid-state lasers which use a crystalline or glass rod which is doped with ions that provide required energy states. The class of lasers include ruby lasers, i.e. based on chromium-doped corundum, yttrium orthovanadate (Nd:YVO$_4$) lasers, yttrium lithium fluoride (Nd:YLF) lasers and yttrium aluminium garnet (Nd:YAG) lasers. Further envisaged are ytterbium lasers such as Yb:YAG, Yb:KGW, Yb:KYW, Yb:SYS, Yb:BOYS, or Yb:CaF$_2$ lasers, or Holmium doped YAG lasers, Yb:YAG lasers. Particularly preferred is an itanium-doped sapphire laser.

Further examples of suitable lasers include fiber lasers where the light is guided due to the total internal reflection in a single mode optical fiber, such as erbium or ytterbium fiber lasers.

Also included are Free-electron lasers (FEL), which generate coherent, high power radiation that is widely tunable.

In a specifically preferred embodiment, the laser is a semiconductor laser type in which an active medium is formed by a p-n junction of a semiconductor diode similar to that found in a light-emitting diode. Typically, such laser diodes are formed by doping thin layers on the surface of a crystal wafer. The crystal may thus be doped to produce an n-type region and a p-type region, one above the other, resulting in a p-n junction, or diode. Examples of suitable laser diodes include double heterostructure lasers, e.g. based on GaAs, or $Al_xGa_{(1-x)}As$; quantum well lasers, e.g. based on gallium nitride-materials; quantum cascade lasers, e.g. lasers using InGaAs/InAlAs material, GaAs/AlGaAs material, InGaAs/AlAsSb material, or InAs/AlSb material; separate confinement heterostructure lasers; or distributed feedback lasers. Further details would be known to the skilled person or can be derived from suitable literature sources such as Richard S. Quimby, Photonics and Lasers: An Introduction, John Wiley & Sons, 2006; or L. A. Coldren and S. W. Corzine, Diode Lasers and Photonic Circuits, In a particularly preferred embodiment, the laser is a Vertical-cavity surface-emitting laser (VCSEL). This laser type shows an optical cavity axis along the direction of current flow. The active region length is short compared with the lateral dimensions so that the radiation emerges from the surface of the cavity rather than from its edge. The VCSEL laser resonator typically comprises two distributed Bragg reflector (DBR) mirrors parallel to the wafer surface with an active region consisting of one or more quantum wells for the laser light generation in between. The planar DBR-mirrors may comprise layers with alternating high and low refractive indices. Each layer may have a thickness of a quarter of the laser wavelength in the material. Normally, high reflectivity mirrors are required in VCSELs to balance the short axial length of the gain region. The upper and lower mirrors may be doped as p-type and n-type materials, forming a diode junction. Alternatively, the p-type and n-type regions may be embedded between the mirrors, requiring a more complex semiconductor process to make electrical contact to the active region. The dielectric mirrors thus typically provide a high degree of wavelength-selective reflectance at the required free surface wavelength $\lambda$ if the thicknesses of alternating layers $d_1$ and $d_2$ with refractive indices $n_1$ and $n_2$ are such that $n_1d_1+n_2d_2=\lambda/2$ which then leads to the constructive interference of all partially reflected waves at the interfaces. VCSELs may emit different wavelength ranges. For example, the emitted wavelength range may be from about 650 nm to 1300 nm. These VCSELs are typically based on gallium arsenide (GaAs) wafers with DBRs formed from GaAs and aluminium gallium arsenide ($Al_xGa_{(1-x)}As$ [x=0-1]). VCSELs may also emit longer wavelengths e.g. from 1300 nm to 2000 nm. These VCSELs are typically composed of indium phosphide, or of a dispersion of silica-based optical fibers.

VCSELs are typically very efficient and only require between 3 and 10 mA to operate. They may tune over 10 to 50 $cm^{-1}$ of wavelengths, have collimated beams and output powers of about 0.5 mW. Due to the tenability of the VCSELs the laser may be used for the selection of different absorption lines. The VCSEL may further allow detection of different absorption lines with a single light source.

In an alternative embodiment, the laser may be Vertical-external-cavity surface-emitting laser (VECSEL). The VECSEL is also a semiconductor laser, which is similar to the VCSEL. In comparison to the VCSEL—in which typically two high-reflecting mirrors are incorporated into the laser structure to form the optical cavity—in a VECSEL one of the two mirrors is external to the diode structure. The cavity may therefore include a free-space region. The external mirror of VECSELs permits a huge area of the diode to participate in generating light in a single mode. This typically results in a higher power than attainable with other laser models.

According to embodiments of the invention, the lasers may emit light as UV A radiation or UV B radiation, as visible radiation or as infrared radiation. The emitted wavelengths may thus be in the range of about 380 to 315 nm (UV-A radiation), in the range of about 315 to 280 nm (UV-B radiation), in the range of about 380 to 780 nm (visible light), or in the range of about 780 nm to 1 mm (infrared light). Preferred are laser diodes, which are of a small size and may advantageously be implemented in a setup according to the present invention.

In specific embodiments, lasers diodes as described herein may additionally comprise modules conveying a temperature stability mechanism (TEC), which allows to compensate for temperature drifts.

It is preferred that a laser as defined herein above emits light of a confined wavelength range, e.g. of which the central wavelength ranges within 343.4 nm ±10 nm, 360.5 nm ±10 nm, 380.2 nm ±10 nm, 446.7 nm ±10 nm, 477.3 nm ±10 nm, 532.2 nm ±10 nm, 630.0 nm ±10 nm, 687.2 nm ±10 nm, 689.3 nm ±10 nm, 760.8 nm ±10 nm, 763.8 nm ±10 nm, or 1065.2 nm ±10 nm.

In a specific embodiment, the VCSEL as defined herein above, is capable of emitting light of a confined wavelength range of 343.4 nm ±10 nm, 360.5 nm ±10 nm, 380.2 nm ±10 nm, 446.7 nm ±10 nm, 477.3 nm ±10 nm, 532.2 nm ±10 nm, 630.0 nm ±10 nm, 687.2 nm ±10 nm, 689.3 nm ±10 nm, 760.8 nm ±10 nm, 763.8 nm ±10 nm, or 1065.2 nm ±10 nm. In a particularly preferred embodiment, the VCSEL as defined herein above, is capable of emitting light of a confined wavelength range, e.g. of which the central wavelength ranges within 687.2 nm ±10 nm, 689.3 nm ±10 nm, 760.8 nm ±10 nm, 763.8 nm ±10 nm. Even more preferred is the emission of light by a VCSEL of a confined wavelength range of which the central wavelength ranges within 760.8 nm ±10 nm.

In a further embodiment, the light source may be a light emitting diode or LED. The term "light emitting diode" as used herein refers a semiconductor light source, in which electrons are able to recombine with holes within a device, thus releasing energy in form of photons. It typically consists of a chip of semiconducting material doped with impurities to create a p-n junction. The LED may be composed of a GaAs AlGaAs, GasP, AlGaInP, GaP, InGaN, GaN, ZnSe, SiC, diamond, boron nitride, AlN, AlGaN, or AlGaInN or any suitable combination or mixture thereof. The LED may emit light of different wavelengths, e.g. in the wavelength range of about 460 to 490 nm (blue LED), in the range of about 490 to 520 nm (cyan LED), in the range of about 520 to 550 nm (green LED), in the range of about 610 to 620 nm (red-orange LED), in the range of about 620 to 645 nm (red LED), or in the wavelength range of about 400 to 700 nm (white LED). The LED used in the context of the present invention may further emit light in the range of about 380 to 315 nm (UV-A radiation), in the range of about 315 to 280 nm (UV-B radiation), or in the range of about 780 nm to 1 mm (infrared light). Further details would be known to the skilled person or can be derived from suitable literature sources such as E. Fred Schubert, Light-Emitting Diodes, Cambridge University Press, 2006.

It is preferred that the LED emits light with the central wavelength locating in the wavelength range, e.g. of 343.4 nm ±10 nm, 360.5 nm ±10 nm, 380.2 nm ±10 nm, 446.7 nm ±10 nm, 477.3 nm ±10 nm, 532.2 nm ±10 nm, 630.0 nm ±10 nm, 687.2 nm ±10 nm, 689.3 nm ±10 nm, 760.8 nm ±10 nm, 763.8 nm ±10 nm, or 1065.2 nm ±10 nm. In a particularly preferred embodiment, the LED as defined herein above, is capable of emitting light with the central wavelength locating in the wavelength range of 687.2 nm ±10 nm, 689.3 nm ±10 nm, 760.8 nm ±10 nm, 763.8 nm ±10 nm. Even more preferred is the emission of light by the LED with the central wavelength locating in the wavelength range of 760.8 nm ±10 nm. In preferred embodiments, the LED provides light with a power of 0.1 mW up to 10 W, e.g. 0.1 mW, 0.2 mW, 0.5 mW, 1 mW, 2 mW, 3 mW, 4 mW, 5 mW, or 10 mW.

The present invention further envisages that the absorption spectroscopy device comprises more than one light source, e.g. two or more lasers or LEDs or a mixture of a laser and a LED. Such multiple light sources may be adapted to the emission of light of different wavelengths, e.g. of light with the central wavelength locating in the wavelength range, e.g. of 343.4 nm ±10 nm, 360.5 nm ±10 nm, 380.2 nm ±10 nm, 446.7 nm ±10 nm, 477.3 nm ±10 nm, 532.2 nm ±10 nm, 630.0 nm ±10 nm, 687.2 nm ±10 nm, 689.3 nm ±10 nm, 760.8 nm ±10 nm, 763.8 nm ±10 nm, or 1065.2 nm ±10 nm.

A "photo-detector" as mentioned above refers to a device for the detection of light. The photo-detector may be provided as single detector, or in the form of one-dimensional or two-dimensional photo-detector arrays. The photo-detector may be sensitive for a broad range of optical wavelengths, for a specific, small range of optical wavelengths, or for a defined single wavelength within a variation of about ±10 nm. In certain embodiments, the photo-detector may be adapted to have zero response in some certain other wavelength ranges. The photo-detector may further be suitable for a range of optical powers. For example, the maximum detected power can be limited e.g. by damage issues or by a nonlinear response, the minimum power may be determined by noise. The photo-detector may further show a dynamic range, i.e. a ratio of maximum and minimum detectable power, of about 10 to 70 dB. According to further embodiments, the photo-detector may be a high quantum efficiency photo-detector. The detection bandwidth of the photo-detector may be in a broad range of 5 Hz to several kHz, or it may be in a narrow frequency range of a 200 Hz, 100 Hz, 50 Hz, 20 Hz etc. Further details would be known to the skilled person or can be derived from suitable literature sources such as Ljubisa Ristic, Sensor Technology & Devices (Optoelectronics Library), Artech House Inc., 1994; or Richard S. Quimby, Photonics and Lasers: An Introduction; John Wiley & Sons, 2006.

Examples of suitable photo-detectors include photodiodes, which are semiconductor devices with a p-n junction or p-i-n structure (i=intrinsic material), where light is absorbed in a depletion region and generates a photocurrent. Photodiodes may be fast, highly linear have a compact form and exhibit a high quantum efficiency (i.e., generate nearly one electron per incident photon) and a high dynamic range. The photodiode may preferably be operated in combination with suitable electronics, which allow for a control of the diode operations. Examples of sensitive photodiodes include avalanche photodiodes.

Further examples include metal-semiconductor-metal (MSM) photo-detectors which typically contain two Schottky contacts instead of a p-n junction. These photo-detector variants are typically faster than photodiodes, with bandwidths up to hundreds of gigahertz.

Further examples include phototransistors, which are structurally similar to photodiodes, but exploit internal amplification of the photocurrent. Another example of a photo-detector is a photo-resistor which may be based on semiconductor materials, e.g. cadmium sulfide (CdS). The photo-resistor may be slower than the photodiode and may not reach its sensitivity. It may exhibit a strong nonlinear response. Yet another example of a suitable photo-detector is a photomultiplier which is based on vacuum tubes. The photomultiplier can exhibit the combination of an extremely high sensitivity with a high speed. Additional examples include pyroelectric photo-detectors which exploit a pyro-electric voltage pulse generated in a nonlinear crystal (e.g. $LiTaO_3$) when heated by absorption of a light pulse on an absorbing coating on the crystal. These detectors may specifically be used for measurement of micro joule pulse energies. The photo-detector may further be a thermal detector. This form typically measures a temperature rise caused by the absorption of light, can be robust and used for the measurement of very high laser powers.

In further embodiments, the more than one photo-detector may be provided or used. For example, if emitted radiation is emitted in more than one specific wavelength, for each wavelength or range of wavelengths a specific photo-detector may be provided.

The present invention preferably envisages that the light source and the photo-detector are comprised within one physical entity, e.g. a laser package group. Such a laser package group advantageously reduces the amount of different elements within the light cavity vessel and in particular reduces the sectors of the light cavity vessel which are not reflective. Thereby the efficiency of reflection and accordingly the efficiency of detection can be increased. A laser package group as mentioned above may be provided in the form of an integrated laser/photo-detector device, e.g. on a semiconductor platform, in particular a silicon based platform. In preferred embodiments the laser package group may have size or dimension which allows to accommodate it in a transistor outline package or TO housing, e.g. comprising a TO header and a TO cap. The laser package may further comprise additional elements such as an internal temperature controller (TEC), and/or a thermistor. Suitable packages are, for example, offered by ULM Photonics, as, e.g. with parameters derivable from http://www.ulm-photonics.com/components/com_products/datasheets/VCSEL-ULM760-SingleMode.pdf.

In further embodiments of the present invention the absorption spectroscopy device may comprise additional functional elements. For example, it may comprise a pressure and temperature sensor. The absorption spectroscopy device may further be equipped with heating or cooling elements to keep the temperature at a predefined value, or with a pressure regulation element in order to provide a pressure according to predefined value. The temperature and pressure in the light cavity vessel may accordingly be set to a predefined value and kept at the value during its operation. Changes to temperature and/or pressure may further be recognized by the sensors, leading to an alert and/or a readjustment of the above mentioned elements to bring the temperature and pressure back to the predefined values. In further embodiments, the absorption spectroscopy device may comprise a gas vacuum pump or exhauster which is capable of removing gas molecules from the light cavity vessel. In further embodiments, the device may comprise a vacuum sensor. In further embodiments, the device may comprise a unit which is adapted to introduce a defined amount of gaseous molecules to the light cavity vessel, e.g. a defined amount of oxygen. This defined amount may be provided in any suitable form, e.g. in a cartridge etc.

In further embodiments of the absorption spectroscopy device may comprise means to control, acquire and process data accumulated by the photo-detector, or by any other unit of the device. A means to control, acquire and process data may be an electronic or computerized module, which is operably linked to the photo-detector, and optionally also to the light source, and/or inlet/outlet elements, and/or temperature or pressure sensors, and/or heating/cooling elements and/or pressure adjustment elements. Furthermore, the device may comprise a suitable control element for the operation of the light source, e.g. the LED or the laser. This control element may be linked to the data accumulation module and/or any other module as defined herein. The control element may be based on digital signal processing elements and implement corresponding suitable algorithms and functions. Operation signals and/or data may further be transferred to the device via suitable data transfer methods, e.g. data cable or WLAN connections. In certain embodiments, the device may be provided as part of a medical or diagnostic system, e.g. hospital system. The device may accordingly be integrated with medical detection or diagnosis devices, e.g. for measuring parameters such a blood pressure, heart rate, pulse etc. The device may further be used as part of respiratory systems or sub-systems, i.e. of respiratory therapy systems. For example, the device may be used as extension or sub-system to respiratory $CO_2$ detection or capnography systems. An example of such a system is the Capnostat 5 $CO_2$ measurement system, offered by respironics, or any future variants thereof. In alternative embodiments, the device may be provided as part of consumer lifestyle systems. For example, it may be provided as integral part or additive module of an air conditioner. The device may accordingly be used to check gas concentrations, e.g. oxygen and/or nitrogen and/or $CO_2$ concentration and/or be linked to the operational control of the air conditioner, e.g. allowing for an adjustment of the air conditioning in dependency of the detected gas concentration, in particular the detected concentration of oxygen.

In further embodiments, the device may be provided as part of an air purifier system. The device may accordingly be used to check gas concentrations, e.g. oxygen and/or nitrogen and/or $CO_2$ concentration and be linked to the operational control of the air purifier, e.g. allowing for an operation of the air purifier when the gas concentration, e.g. oxygen concentration, passes a predefined threshold value, or if specific gases are detected. In further embodiments, the absorption spectroscopy device may be provided in a gas tight surrounding or housing. Preferably, the light cavity vessel as defined herein above may be provided in a sealed manner so that during the operation no gas can enter or exit the cavity vessel. The device may further comprise technical means to detect the whether the light cavity vessel is gas tight, i.e. whether there is any leakage of gas, in particular oxygen.

The absorption measurement for which a device according to the present invention is adapted includes the use of a light source and photo-detector as defined above. The measurement may be based on an implementation of Lambert-Beer's law, i.e. a line-of-sight technique, in which the absorbance (ratio of the change in light intensity to the incident light intensity) are spatial integrals along the optical path. Typically, the quantity measured is the ratio of incident light intensity to transmitted light intensity, thus resulting in an independence of the measurement of any laser intensity fluctuations. The measured light intensity ($I_{cavity}$) follows the principle $$I_{cavity}(1) = I_0 e^{-\sigma n L} \times \frac{1}{1 - \exp(-\sigma n L)\eta} \qquad \text{Formula (2)}$$

where $\sigma$ is the absorption cross section of a gas molecules at the given wavelength, n is the concentration of the gas molecules, L is the effective geometric length of the light cavity vessel, which is approximately the same as the diameter of the vessel when it is in a circular form and $\eta$ is the reflectivity ($0<\eta<1$) of the reflective layer of the inner wall of the vessel. However, in contrast to a single path absorption, whose measured laser intensity follows the principle $$I_{cavity}(1') = I_0 e^{-\sigma n L} \qquad \text{Formula (3)}$$

the device according to the present invention allows to achieve higher absorbance, which results in a lower detection limit of the gas molecule's concentration.

In case the measurement is performed at two distinct wavelengths, i.e. an absorption wavelength and a control wavelength, e.g. on the basis of two distinct light sources or on the basis of a tunable light source which is capable of emitting two distinct wavelengths, the measurement of the control wavelength may be based on the formula depicted below. In particular, the measured laser intensity of the control, non-absorption wavelength may be determined according to:

$$I_{cavity}(2) = I_0 \times \frac{1}{1 - \eta} \qquad \text{Formula (4)}$$

By comparing the change in these intensities, i.e. by comparing $I_{(cavity)}(1)$ and $I_{(cavity)}(2)$ the concentration n may be determined.

The gas to be measured may be any gas which shows a light absorption in the range of wavelengths as produced by lights sources defined herein. The gas to be measured may be a gaseous material at ambient temperatures (e.g. 5 to 30° C.), or it may be a material which becomes gaseous upon heating or evaporation. In preferred embodiments, the gaseous material may comprise gaseous molecules found in an ambient atmosphere, e.g. $O_2$, $N_2$, $CH_4$, $CO_2$, CO, NO. Further details on the gaseous material to be measured and their particulars, e.g. the specific measurement conditions or wavelengths at which the measurements should be carried out etc. may be derived from suitable literature sources, for example from John H. Seinfeld and Spyros N. Pandis, Atmospheric Chemistry and Physics: From Air Pollution to Climate Change, John Wiley & Sons, 2006.

FIG. 1 shows schematically an absorption spectroscopy device according to the present invention. The absorption spectroscopy device comprises a light cavity vessel 1. The absorption spectroscopy device further comprises an inner wall coated by a reflective layer 2. The absorption spectroscopy device is additionally equipped with a light source in the form of a VCSEL laser 3. This light source may further comprise a photodetector, e.g. in a packaged form. The VCSEL laser 3 is capable of emitting radiation 4, which is reflected multiple times by the reflective layer of the inner wall of the cavity vessel (2) and eventually may be detected by the photodetector. This principle can be used for the measurement of gas in the cavity vessel (1).

In a further aspect the invention relates to a method for spectroscopically measuring the concentration of a gas comprising the steps:
(a) emitting light radiation which passes through a light cavity vessel comprising the gas, wherein said light radiation is at least partially reflected by the inner wall of said cavity vessel;
(b) detecting at least a portion of the emitted light with a photo-detector;
(c) determining radiation absorption of said gas on-airway by comparison of the detected light with a reference measurement carried out according to steps (a) and (b).

Within this method the light cavity vessel to be used is preferably a light cavity vessels as defined herein above. The inner wall of the light cavity vessel may be at least partially be coated with a light reflective layer, e.g. a distributed Bragg reflector or a brilliant metal coating, e.g. as defined herein above.

Further, the detection preferably carried out with a photodetector as defined herein above. The emission of light radiation may be performed by a LED or laser, preferably by a laser, more preferably by a VCSEL, e.g. as defined herein above.

The determination of the radiation absorbance may in principle be performed by comparing the absorbance in a gas-filled light cavity vessel of the light emitted from the light source and detected by the photo-detector, which follows the Lambert-Beer law, with the absorbance of light in said light cavity vessel emitted from a light source and detected by said photo-detector under suitable control conditions.

Such suitable control conditions can, for example, be reference measurements with the same light cavity vessel which is used for the detection of gas. The light cavity vessel may, for example, be provided without the gas to be measured, in particular without oxygen. In specific embodiments, the cavity vessel may be provided in vacuum, i.e. without any gas. The determination of the radiation absorbance under these conditions may be registered and suitably saved as reference absorbance for future measurements with gas molecules being present. The background or noise absorbance measured in such a step may preferably be subtracted from any measured radiation absorbance under conditions, in which gas is present in the light cavity vessel, e.g. conditions in which oxygen is present.

In further embodiments, a control measurement may be used for calibration of the method. For this purpose the light cavity vessel may be filled with a defined amount of gas. Subsequently, the radiation absorbance may be determined, registered and suitably saved as reference absorbance for future measurements with arbitrary amounts of gaseous materials, in particular with arbitrary amounts of the same gaseous materials. The measured absorbance may preferably be corrected by the above described background or noise absorbance determined in vacuum, i.e. the background or noise absorbance may be subtracted from the measured absorbance in the presence of a defined amount of gas. This calibration step may, in specific embodiments, be carried out with 1, 2, 3, 4, 5, 6 or more different amounts of the gas, e.g. oxygen, in order to increase the accuracy of the method and to minimize measuring errors.

Reference measurements in vacuum and/or in the presence of a defined amount of gas may be stored for future measurements of the same light cavity vessel. These values may, for example, be provided together with the light cavity vessel in the form of a electronically saved set of data present in a data collection or operation module of a device as defined herein above, or provided via a connection of the device with external databases etc.

In further embodiments of the present invention, the control may be performed by comparing two different wavelength measurements. One measurement may be carried out at a wavelength which does not lead to absorbance by the molecule whose concentration is to be determined, while the other measurement may be carried out with said molecule. If for the control a wavelength is used, which is very similar to the detection wavelength, the control absorption may be determined according to a comparison of the value determined by formula (3) with the value determined by formula (2).

In a preferred embodiment of the method according to the present invention, the light radiation to be used for the method according to the present invention is a radiation from a light emitting diode or laser around the wavelength of 687.2 nm, 689.3 nm, 760.8 nm, or 763.8 nm within the variation of the wavelength of ±10 nm. In a particularly preferred embodiment, light radiation is a laser radiation of a confined wavelength range of 687.2 nm ±10 nm, 689.3 nm ±10 nm, 760.8 nm ±10 nm, 763.8 nm ±10 nm. Even more preferred is the emission of light by a VCSEL of a confined wavelength range of 760.8 nm ±10 nm.

In a particularly preferred embodiment of the present invention, the method is carried out in a device as described herein above.

The following FIGURE is provided for illustrative purposes. It is thus understood that the figure is not to be construed as limiting. The skilled person in the art will clearly be able to envisage further modifications of the principles laid out herein.

The invention claimed is:

1. An absorption spectroscopy device, comprising:
a light cavity vessel, whose inner wall is at least partially light reflective, and wherein said inner wall of the light cavity vessel is at least partially coated with light a reflective layer, the light cavity vessel being a gas tight vessel that is sealed so that during operation no gas can enter or exit the cavity vessel;
a photo-detector; and
a light source,
wherein said light source is capable of emitting light radiation which passes through said light cavity vessel, wherein said light cavity vessel is capable of reflecting the emitted radiation and wherein said photo-detector is capable of detecting at least a portion of the emitted light,
and wherein said light reflective layer is a distributed Bragg reflector.

2. The absorption spectroscopy device of claim 1, wherein said light source is at least one of a light emitting diode or a laser.

3. The absorption spectroscopy device of claim 1, wherein said distributed Bragg reflector comprises layers of SiC and MgO; SiC and Silica; GaAs and AlAs; ITO; or a-Si and a-Si.

4. The absorption spectroscopy device of claim 1, wherein said distributed Bragg reflector is reflective for the radiation corresponding to the electronic transitions of oxygen molecules from the ground electronic state (X $^3\Sigma_g^-$) to the electronic excited states (a $^1\Delta_g$, b $^1\Sigma_g^{30}$), wherein the wavelength of said radiation is at about 343.4 nm, 360.5 nm, 380.2 nm, 446.7 nm, 477.3 nm, 532.2 nm, 630.0 nm, 687.2 nm, 689.3 nm, or 1065.2 nm as the center wavelength within a variation of the wavelength of ±10 nm.

5. The absorption spectroscopy device of the claim 1, wherein said light source is a light emitting diode or a laser diode of UV-A radiation, UV-B radiation, visible radiation or infrared radiation.

6. The absorption spectroscopy device of claim 1, wherein said light source is a vertical-cavity surface-emitting laser (VCSEL) diode.

7. The absorption spectroscopy device of claim 6, wherein said VCSEL diode emits laser radiation around the wavelength of about 687.2 nm, 689.3 nm, within the variation of the wavelength of ±10 nm.

8. The absorption spectroscopy device of claim 6, wherein said VCSEL diode is part of a laser package, the laser package further including a photodiode as an integrated element with the VCSEL diode.

9. The absorption spectroscopy device of claim 1, wherein said device is adapted to measure $O_2$.

10. A method for spectroscopically measuring the concentration of $O_2$, comprising:
   emitting light radiation which passes through a light cavity vessel comprising the gas, wherein said light radiation is at least partially reflected by the inner wall of said cavity vessel;
   detecting at least a portion of the emitted light with a photodetector;
   determining radiation absorption of said gas on-airway by comparison of the detected light with a reference measurement carried out according to the preceeding steps with (i) a defined amount of said gas and (ii) without said gas, wherein said method is carried out in a device as defined in claim 1.

11. The method of claim 10, wherein said light radiation is the radiation from a light emitting diode or laser around the wavelength of 687.2 nm or 689.3 nm within the variation of the wavelength of ±10 nm.

12. The method of claim 10, wherein said reference measurements are linked to the specific device in which they were carried out; and are optionally stored for further gas concentration measurements according to the emitting and detecting steps.

13. The absorption spectroscopy device of claim 1 wherein the light cavity vessel is a spherical light cavity vessel having the shape of a sphere and the inner wall is an inner wall of the sphere.

14. The absorption spectroscopy device of claim 1 wherein the inner wall of the light cavity vessel has no edges or angles.

15. The absorption spectroscopy device of claim 1 wherein curvature of the inner wall of the light cavity vessel produces multiple reflections of the emitted radiation effective for the emitted radiation to fill the geometric space of the light cavity vessel.

16. The absorption spectroscopy device of claim 1 wherein the light source is integrated with the photo-detector.

17. An absorption spectroscopy device, comprising:
   a light cavity vessel having a curved inner wall that is at least partially light reflective, wherein the curved inner wall of the light cavity vessel is at least partially coated with a light reflective layer, the light cavity vessel being a gas tight vessel that is sealed so that during operation no gas can enter or exit the cavity vessel;
   a light source arranged to emit light radiation into the light cavity vessel where multiple reflections of the light radiation off the curved inner wall of the light cavity vessel causes the light radiation to fill the geometric space of the light cavity vessel; and
   a photo-detector arranged to detect a portion of the light radiation filling the geometric space of the light cavity vessel that hits the photo-detector.

18. The absorption spectroscopy device of claim 17 wherein the light cavity vessel is a spherical light cavity vessel.

19. The absorption spectroscopy device of claim 17 wherein the curved inner wall of the light cavity vessel has no edges or angles.

* * * * *